(12) United States Patent
Mitchell

(10) Patent No.: US 7,231,304 B2
(45) Date of Patent: Jun. 12, 2007

(54) INTERFERENCE PATTERN TESTING OF MATERIALS

(75) Inventor: Michael D. Mitchell, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 118 days.

(21) Appl. No.: 11/173,700

(22) Filed: Jun. 30, 2005

(65) Prior Publication Data

US 2007/0005269 A1    Jan. 4, 2007

(51) Int. Cl.
*G06F 15/00* (2006.01)

(52) U.S. Cl. .......................... 702/35; 356/512
(58) Field of Classification Search ............... 702/35; 356/512

See application file for complete search history.

(56) References Cited

U.S. PATENT DOCUMENTS

2006/0187465 A1 * 8/2006 De Groot .................. 356/512

* cited by examiner

*Primary Examiner*—Edward Raymond
(74) *Attorney, Agent, or Firm*—Lee & Hayes, PLLC

(57) ABSTRACT

Methods, systems, and articles of manufacture consistent with the present invention identify a flaw in a structure by comparing a first interference pattern resulting from a first wave signal and a second wave signal propagating through the structure to a second interference pattern resulting from the first wave signal and the second wave signal propagating through the structure. The second interference pattern is obtained after obtaining the first interference pattern. It is determined whether there is a flaw in the structure by determining whether the first interference pattern deviates from the second interference pattern by a predetermined variance.

18 Claims, 3 Drawing Sheets

INTERFERENCE PATTERN TESTING OF MATERIALS

BACKGROUND OF THE INVENTION

The present invention generally relates to the field of material testing and, more particularly, to methods and systems for detecting flaws in structures using vibratory waves.

Testing the health of structures, such as composite-material structures used in aircraft manufacturing, typically has been a time consuming and costly endeavor. To reduce testing time, the aircraft manufacturing industry, for example, has been searching for methods of globally rather than locally testing of aircraft sub-assemblies. A conventional approach used to globally test composite structures requires excitation of a structure with a vibratory wave and monitoring the response of the structure in the frequency domain. This conventional approach typically requires considerable power for exciting the structure and also extensive time for analyzing the response spectrum.

The conventional approach is further complicated by an exhibited property called "acoustoelasticity." The frequency response of the structure under test may change with a change in strain within the structure. Variables, such as temperature, torque specifications, part orientation, and weight on the structure may change the internal strain of the structure and thus change its frequency response. Using the conventional approach, it is nearly impossible to distinguish a flaw in a structure from a change in internal strain in the structure.

SUMMARY OF THE INVENTION

Methods, systems, and articles of manufacture consistent with the present invention test the health of a structure using wave interference patterns. A vibratory wave is introduced into the structure at two or more locations. A sensor picks up vibrations in the structure, and the vibrations are converted to digital measured data. As patterns of destructive and nondestructive interference occur in the structure from the vibrations, changes in the integrity of the structure are manifested in changes in the measured interference patterns. As the wave propagates through the structure, its velocity changes due to inconsistencies, such as flaws in the structure. These changes in velocity change the interference patterns detected by the sensor. Therefore, if no flaws are introduced into the structure, the measured interference patterns will be substantially constant for subsequent measurements. Methods, systems, and articles of manufacture consistent with the present invention can identify a flaw by determining whether the difference between the measured data and the baseline measured data exceeds a predetermined value.

Since methods and systems consistent with the present invention do not rely on introducing waves into a structure to observe its resonant response, less power is required compared to conventional approaches. Further, methods and systems consistent with the present invention are not affected by changing material response due to internal strain in a structure. Therefore, unlike conventional approaches, invalid flaw detection due to changing frequency response is avoided. Further, since measurement and analysis are performed in the time domain, results can be obtained on the fly instead of having to spend large amounts of time analyzing frequency response characteristics.

In accordance with methods consistent with the present invention, a method in a data processing system having a program for identifying a flaw in a structure is provided. The method comprises the steps of: comparing a first interference pattern resulting from a first wave signal and a second wave signal propagating through the structure to a second interference pattern resulting from the first wave signal and the second wave signal propagating through the structure, the second interference pattern being obtained after obtaining the first interference pattern; and determining whether there is a flaw in the structure by determining whether the first interference pattern deviates from the second interference pattern by a predetermined variance.

In accordance with articles of manufacture consistent with the present invention, a computer-readable medium containing instructions that cause a data processing system having a program to perform a method for identifying a flaw in a structure is provided. The method comprises the steps of: comparing a first interference pattern resulting from a first wave signal and a second wave signal propagating through the structure to a second interference pattern resulting from the first wave signal and the second wave signal propagating through the structure, the second interference pattern being obtained after obtaining the first interference pattern; and determining whether there is a flaw in the structure by determining whether the first interference pattern deviates from the second interference pattern by a predetermined variance.

In accordance with systems consistent with the present invention, a data processing system for identifying a flaw in a structure is provided. The data processing system comprises: a memory having a program that: compares a first interference pattern resulting from a first wave signal and a second wave signal propagating through the structure to a second interference pattern resulting from the first wave signal and the second wave signal propagating through the structure, the second interference pattern being obtained after obtaining the first interference pattern; and determines whether there is a flaw in the structure by determining whether the first interference pattern deviates from the second interference pattern by a predetermined variance; and a processing unit that runs the program.

In accordance with systems consistent with the present invention, a data processing system for identifying a flaw in a structure is provided. The data processing system comprises: means for comparing a first interference pattern resulting from a first wave signal and a second wave signal propagating through the structure to a second interference pattern resulting from the first wave signal and the second wave signal propagating through the structure, the second interference pattern being obtained after obtaining the first interference pattern; and means for determining whether there is a flaw in the structure by determining whether the first interference pattern deviates from the second interference pattern by a predetermined variance.

Other features of the invention will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The accompanying drawings, which are incorporated in and constitute a part of this specification, illustrate an implementation of the invention and, together with the description, serve to explain the advantages and principles of the invention. In the drawings.

Corresponding reference characters indicate corresponding parts throughout the several views of the drawings.

DETAILED DESCRIPTION OF THE INVENTION

Reference will now be made in detail to an implementation in accordance with methods, systems, and articles of manufacture consistent with the present invention as illustrated in the accompanying drawings.

Figure 1:
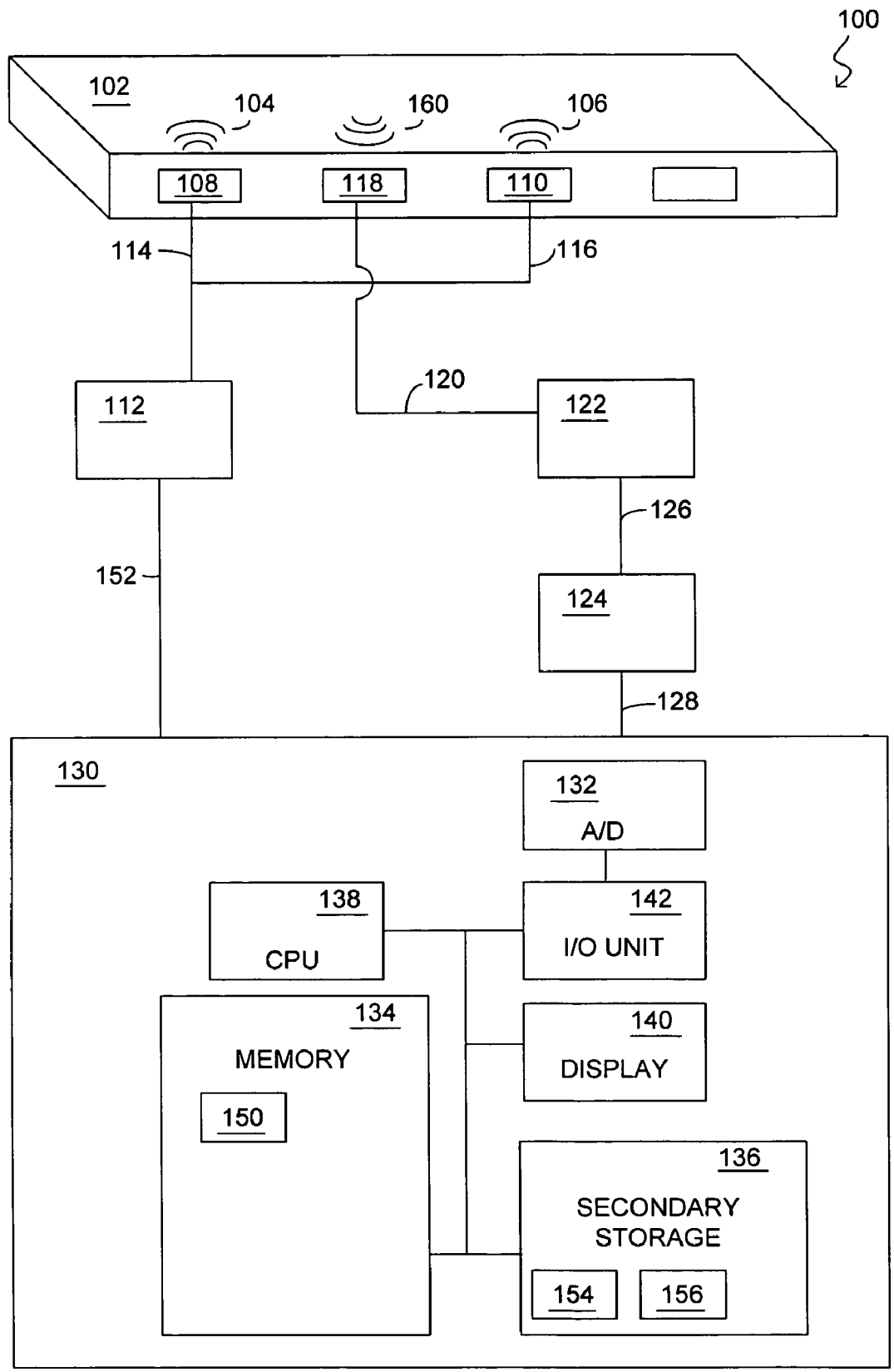
FIG. 1 is a schematic diagram of a system for identifying a flaw in a structure consistent with the present invention.

Methods, systems, and articles of manufacture consistent with the present invention test structural health using wave interference patterns. FIG. 1 depicts a block diagram of a system 100 for testing the structural health of a structure 102 consistent with the present invention. The structure can comprise any suitable material, including composite materials. In the illustrative embodiment, the structure is carbon fiber composite beam. A first wave 104 and a second wave 106 are introduced into the structure via a first actuator 108 and a second actuator 110, respectively. In the illustrative example, the first and second actuators receive similar electronic test signals that are sine waves having a predetermined amplitude and frequency, such as 3 Volts at 5250 Hertz. The first and second actuators convert the electronic test signals into mechanical energy, which is transmitted into the structure as the first and second waves. In the illustrative example, the first and second actuators are piezoelectric actuators that are bonded to the structure. The illustrative piezoelectric actuators are Model No. QP-10 actuators manufactured by Mide Technology Corporation of Medford, Mass. One having skill in the art will appreciate that different types of actuators and a different number of actuators can be used. Further, the electronic test signals that are converted into mechanical energy by the actuators can have different characteristics than those in the illustrative example. For example, the electronic test signals do not have to be sign waves and can have different amplitude and frequency characteristics than those identified above. Further, the test signals are not required to have similar characteristics with respect to each other.

The test signals are generated by a signal generator 112. In the illustrative example, the signal generator is a Model No. HP 3314A, which is manufactured by Hewlitt-Packard Company of Palo Alto, Calif. The signal generator generates a burst of four cycles of a 3 Volt peak sine wave having a frequency of 5250 Hertz in the illustrative example. The test signal travels along a first lead 114 to the first actuator and along a second lead 116 to the second actuator. The first and second actuators convert the test signals into mechanical energy, which is transmitted into the structure as the first and second waves. As the first and second waves transmit through the structure, they interact with the structure and with each other. For example, each wave may experience changes in velocity at material boundaries. Further, a wave's amplitude is affected by destructive and nondestructive interference caused by interaction with the structure, other waves, or with components of itself that have been reflected from material boundaries.

One or more sensors, such as sensor 118, detect mechanical vibrations 160 in the structure. In the illustrative example, sensor 118 is a piezoelectric actuator such as the ones used for the first and second actuators, however, alternative sensors may be used. Sensor 118 detects mechanical vibrations in the structure and converts the mechanical vibrations into an electronic measured signal. The measured signal is transmitted via a measure signal lead 120 to a filter 122, which may reject D.C. offset and ambient-induced noise in the measured signal. In the illustrative example, the filter is a band pass filter centered about the frequency of the test signal. The filter outputs a filtered measurement signal, which is received by an isolation amplifier 124 having an input terminal electrically coupled via a lead 126 to an output terminal of the filter. The isolation amplifier amplifies the filtered measurement signal, for example to 100 times its original amplitude. The construction and implementation of filters and isolation amplifiers are known in the art and will not be discussed in more detail herein.

An output terminal of the isolation amplifier is coupled via lead 128 to an input terminal of a data acquisition system 130. The data acquisition system 130 has an analog-to-digital converter 132 that converts the measured signal to a digital signal. Once the signal is in a digital form, it can be processed by the data processing system 130. Collected measurement data may be archived in a memory 134 or a secondary storage 136 of the data processing system.

Data processing system 130 comprises a central processing unit (CPU) or processor 138, a display device 140, an input/output (I/O) unit 142, secondary storage device 136, and memory 134. The data processing system may further comprise standard input devices such as a keyboard, a mouse or a speech processing means (each not illustrated).

Memory 134 comprises a program 150 that can compare the measured signal to a previously-measured baseline measured signal, which has been stored, to determine whether damage has occurred in the structure. In the illustrative example, program 150 is implemented using Lab VIEW™ software, however, the program can be implemented using another application program or another programming language. LabVIEW is a trademark of National Instruments Corporation of Austin, Tex. As will be described in more detail below, the data acquisition system receives the filtered and amplified measured signal from the isolation amplifier and can store and process the measured signal. The program can compare the measured signal to the previously-measured baseline measured signal to determine whether a flaw has occurred in the structure. The flaw can be any change introduced into the structure, such as a crack, decomposition, delamination, or fatigue.

One having skill in the art will appreciate that the program can reside in memory on a system other than data processing system 130. The program may comprise or may be included in one or more code sections containing instructions for performing their respective operations. Although the program is described as being implemented as software, the present implementation may be implemented as a combination of hardware and software or hardware alone. Also, one having skill in the art will appreciate the program may comprise or may be included in a data processing device, which may be a client or a server, communicating with data processing system 130. Further, one having skill in the art will appreciate that two or more of the signal generator, the filter, the isolation amplifier, and the data processing system can be included in a single device. In the illustrative example, the data processing system comprises a Model No.

AT MIO16-E PC card manufactured by National Instruments Corporation of Austin, Tex.

Although aspects of methods, systems, and articles of manufacture consistent with the present invention are depicted as being stored in memory, one having skill in the art will appreciate these aspects may be stored on or read from other computer-readable media, such as secondary storage devices, like hard disks, floppy disks, and CD-ROM; a carrier wave received from a network such as the Internet; or other forms of ROM or RAM either currently known or later developed. Further, although specific components of data processing system 130 have been described, one having skill in the art will appreciate a data processing system suitable for use with methods, systems, and articles of manufacture consistent with the present invention may contain additional or different components.

Data processing system 130 can itself also be implemented as a client-server data processing system. In that case, program 150 can be stored on the data processing system as a client, and some or all of the steps of the processing described below can be carried out on a remote server, which is accessed by the client over a network. The remote server can comprise components similar to those described above with respect to the data processing system, such as a CPU, an I/O, a memory, a secondary storage, and a display device.

Figure 2:
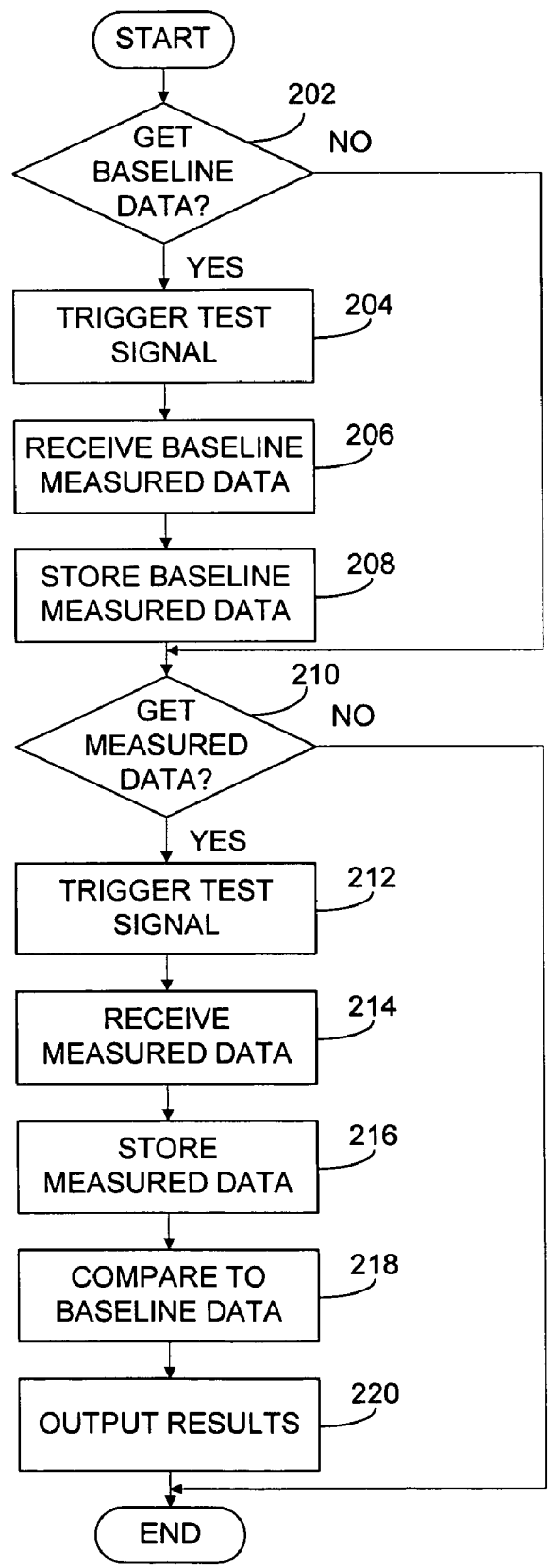
FIG. 2 is a flow diagram of the exemplary steps for identifying a flaw in a structure consistent with the present invention.

FIG. 2 depicts a flow diagram illustrating the exemplary steps performed by program 150 for detecting damage in the structure. As will be described in more detail below, the program compares measured data for the structure to baseline measured data to determine whether there are flaws in the structure. To obtain the measured data, a wave is introduced into the structure at two or more locations by the signal generator, and the measured data comprises patterns of destructive and nondestructive interference that occur in the structure. The measured data is recorded and compared to baseline measured data. Changes in the integrity of the structure are manifested in changes in the measured interference patterns. Structural flaws can be local areas of different density in the structure, and change the velocity of waves propagating through the structure. These changes in velocity change the interference patterns detected by the sensor. Therefore, if no flaws are introduced into the structure, the interference patterns remain substantially constant for subsequent measurements. Although there may be no flaws in the structure, the interference patterns may exhibit some variance due to, for example, jitter when taking measurements. Therefore, the program can identify a flaw by determining whether the difference between the measured data and the baseline measured data exceeds a predetermined variance.

First, the program determines whether to obtain baseline measurement data (step 202). If the program is to obtain baseline measured data, the program effects the data processing system to send a trigger signal via lead 152 to the signal generator (step 204). In turn, the signal generator transmits the test signal to the structure. In the illustrative embodiment, the test signal is a four-cycle burst sine wave with a peak amplitude of 3 Volts and a frequency of 5250 Hertz. The first and second actuators convert the test signal into first and second waves that are introduced into the structure. As the first and second waves transmit through the structure, they interact with the structure and with each other. For example, each wave may experience changes in velocity at material boundaries. Further, a wave's amplitude is effected by destructive and nondestructive interference caused by interaction with other waves or with components of itself that have been reflected from material boundaries. When sensor 118 detects mechanical vibrations in the structure and converts the vibrations into the measured signal, the interference pattern is manifested in the measured signal. Significantly, if no flaws are introduced into the structure, the interference pattern will remain the same or substantially the same for subsequent measurements. It is possible the interference patterns will not be exactly the same, even though no flaw has been introduced into the structure, due to, for example, jitter when taking measurements. Therefore, methods, systems, and articles of manufacture consistent with the present invention determine whether the difference between the measured data and the baseline measured data exceeds a predetermined variance.

The measured signal arrives at the data processing system, where it is converted to a digital signal by the analog-to-digital converter (step 206) and stored as a baseline measured data file 154 in the secondary storage (step 208). Alternatively, the baseline measured data can be stored in another location, such as in the memory.

Then, the program determines whether to obtain new measured data (step 210). If new measured data is to be obtained, the program effects the data processing system to send a trigger signal to the signal generator (212). As described above with respect to obtaining the baseline measured data, the signal generator transmits a test signal, which is introduced into the structure as first and second waves. The sensor detects mechanical vibrations in the structure and converts the vibrations into a measured signal, which is transmitted to the data processing system. The data processing system receives the measured signal and converts the measured signal to digital measured data (step 214). Then, the program stores the measured data into a measured data file 156 in the secondary storage. Alternatively, the measured data file can be stored in another location, such as in memory.

To determine whether there is a flaw in the structure, the program compares the measured data in the measured data file to the previously-stored baseline measured data in the baseline measured data file (step 218). More specifically, the measured data file and the baseline measured data file each can include a same number of sample data points. The sample data points in each file are obtained by the data processing system at the data rate. Therefore, corresponding data points in each file correspond in the time domain. Since the interference pattern manifested in the measured data is repeatable for subsequent measurements when no flaw is introduced into the structure, the amplitude at each respective data point remains substantially the same for subsequent measurements, but may vary slightly due to, for example, jitter in the measurements. For example, in a case where the baseline and subsequently measured data files each contain 500 data points, the data values (i.e., the signal amplitudes) at the corresponding data points in the files will be substantially the same, but may vary slightly due to jitter. That is the data values may not be exactly the same due to minor errors introduced into the measured signal. Therefore, when the program compares each data point of the measured data to corresponding data points in the baseline measured data to identify a flaw, the program determines whether there is a difference in the data values exceeding a predetermined variance.

Table 1 includes illustrate data for a case in which no flaw has been introduced into the structure. The two left columns include baseline measured data for a certain number of data points. The two middle columns include measured data for corresponding data points. And the two right columns show the difference in amplitudes for the corresponding data points.

TABLE 1

| Baseline measured data | | Measured data | | Changes | |
|---|---|---|---|---|---|
| Data point | Amplitude | Data point | Amplitude | Data point | Amplitude |
| 0 | 0 | 0 | 0 | 0 | 0 |
| 56 | 1.079 | 56 | 1.055 | 56 | 0.024 |
| 69 | 2.207 | 69 | 2.236 | 69 | −0.029 |
| 83 | 2.788 | 83 | 2.812 | 83 | −0.024 |
| 96 | 3.062 | 96 | 3.057 | 96 | 0.005 |
| 110 | 5.068 | 110 | 5.059 | 110 | 0.009 |
| 123 | 4.668 | 123 | 4.668 | 123 | 0 |
| 137 | 5.376 | 137 | 5.371 | 137 | 0.005 |
| 149 | 3.237 | 149 | 3.228 | 149 | 0.009 |
| 162 | 2.983 | 162 | 2.974 | 162 | 0.009 |
| 173 | 2.026 | 173 | 1.973 | 173 | 0.053 |
| 187 | 1.914 | 187 | 1.88 | 187 | 0.034 |
| 203 | 1.641 | 203 | 1.631 | 203 | 0.01 |
| 218 | 2.725 | 218 | 2.695 | 218 | 0.03 |
| 231 | 4.189 | 231 | 4.146 | 231 | 0.043 |
| 244 | 4.263 | 244 | 4.268 | 244 | −0.005 |
| 258 | 3.96 | 258 | 3.936 | 258 | 0.024 |
| 272 | 5.2 | 272 | 5.166 | 272 | 0.034 |
| 286 | 6.45 | 286 | 6.392 | 286 | 0.058 |
| 299 | 6.494 | 299 | 6.455 | 299 | 0.039 |
| 314 | 4.043 | 314 | 4.023 | 314 | 0.02 |
| 331 | 2.261 | 331 | 2.202 | 331 | 0.059 |
| 346 | 2.129 | 346 | 2.09 | 346 | 0.039 |
| 361 | 3.076 | 361 | 3.052 | 361 | 0.024 |
| 377 | 3.198 | 377 | 3.203 | 377 | −0.005 |
| 391 | 3.848 | 391 | 3.838 | 391 | 0.01 |
| 406 | 3.54 | 406 | 3.481 | 406 | 0.059 |
| 420 | 2.48 | 420 | 2.456 | 420 | 0.024 |
| 434 | 2.837 | 434 | 2.817 | 434 | 0.02 |
| 447 | 3.101 | 447 | 3.101 | 447 | 0 |
| 459 | 2.354 | 459 | 2.339 | 459 | 0.015 |
| 471 | 1.689 | 471 | 1.675 | 471 | 0.014 |
| 483 | 2.588 | 483 | 2.451 | 483 | 0.137 |

In the illustrative example of Table 1, the program determines whether there is a flaw by determining whether peak amplitudes and their locations in time exceed a predetermined statistical variance. For example, the program may determine whether the peak amplitudes vary by more than 0.2 volts. In addition, the program may take into consideration a statistical variance of the data points in time to account for jitter, for example. Since none of the changes in peak amplitudes exceed 0.2 Volts, the program determines that no flaw has been introduced into the sample since the baseline measured data was obtained.

Table 2 includes illustrate data for another case in which a flaw has been introduced into the structure since the baseline measured data has been obtained. Similar to Table 1: the two left columns include baseline measured data for a certain number of data points; the two middle columns include measured data for corresponding data points; and the two right columns show the difference in amplitudes for the corresponding data points.

TABLE 2

| Baseline measured data | | Measured data | | Changes | |
|---|---|---|---|---|---|
| Data point | Amplitude | Data point | Amplitude | Data point | Amplitude |
| 17 | 0.254 | 17 | 0.2 | 17 | 0.054 |
| 29 | 0.474 | 29 | 0.615 | 29 | −0.141 |
| 40 | 0.957 | 40 | 0.972 | 40 | −0.015 |

TABLE 2-continued

| Baseline measured data | | Measured data | | Changes | |
|---|---|---|---|---|---|
| Data point | Amplitude | Data point | Amplitude | Data point | Amplitude |
| 50 | 1.133 | 50 | 0.996 | 50 | 0.137 |
| 63 | 2.856 | 63 | 3.384 | 63 | −0.528 |
| 83 | 6.216 | 83 | 6.68 | 83 | −0.464 |
| 98 | 5.127 | 98 | 4.17 | 98 | 0.957 |
| 118 | 3.247 | 118 | 2.529 | 118 | 0.718 |
| 132 | 1.87 | 132 | 0.908 | 132 | 0.962 |
| 146 | 0.161 | 146 | 1.909 | 146 | −1.748 |
| 158 | 3.794 | 158 | 4.38 | 158 | −0.586 |
| 170 | 3.799 | 170 | 2.554 | 170 | 1.245 |
| 184 | 1.27 | 184 | 1.348 | 184 | −0.078 |
| 202 | 3.198 | 202 | 3.403 | 202 | −0.205 |
| 214 | 3.105 | 214 | 2.603 | 214 | 0.502 |
| 225 | 2.388 | 225 | 2.563 | 225 | −0.175 |
| 237 | 5.322 | 237 | 6.25 | 237 | −0.928 |
| 250 | 3.13 | 250 | 1.196 | 250 | 1.934 |
| 260 | 2.559 | 260 | 3.135 | 260 | −0.576 |
| 273 | 4.053 | 273 | 3.794 | 273 | 0.259 |
| 285 | 4.126 | 285 | 4.131 | 285 | −0.005 |
| 297 | 4.502 | 297 | 5.435 | 297 | −0.933 |
| 310 | 5.376 | 310 | 4.429 | 310 | 0.947 |
| 323 | 0.864 | 323 | 0.991 | 323 | −0.127 |
| 332 | 2.222 | 332 | 1.865 | 332 | 0.357 |
| 343 | 1.016 | 343 | 1.406 | 343 | −0.39 |
| 357 | 2.319 | 357 | 1.509 | 357 | 0.81 |
| 370 | 2.007 | 370 | 1.611 | 370 | 0.396 |
| 381 | 0.957 | 381 | 2.393 | 381 | −1.436 |
| 394 | 1.123 | 394 | 2.783 | 394 | −1.66 |
| 406 | 2.163 | 406 | −0.107 | 406 | 2.27 |
| 416 | 2.305 | 416 | 3.462 | 416 | −1.157 |
| 429 | 4.521 | 429 | 3.311 | 429 | 1.21 |
| 441 | 0.962 | 441 | 1.45 | 441 | −0.488 |
| 452 | 3.369 | 452 | 4.614 | 452 | −1.245 |
| 466 | 2.817 | 466 | 2.676 | 466 | 0.141 |
| 481 | 1.748 | 481 | 0.312 | 481 | 1.436 |
| 490 | 0.942 | 490 | 1.484 | 490 | −0.542 |

In the illustrative example of Table 2, the program determines whether there is a flaw by determining whether the differences in peak amplitudes exceed a predetermined variance. Since several of the peak amplitudes vary by more than a predetermined amount of 0.2 Volts, the program determines a flaw has bee introduced into the sample since the baseline measured data was obtained.

Figure 3:
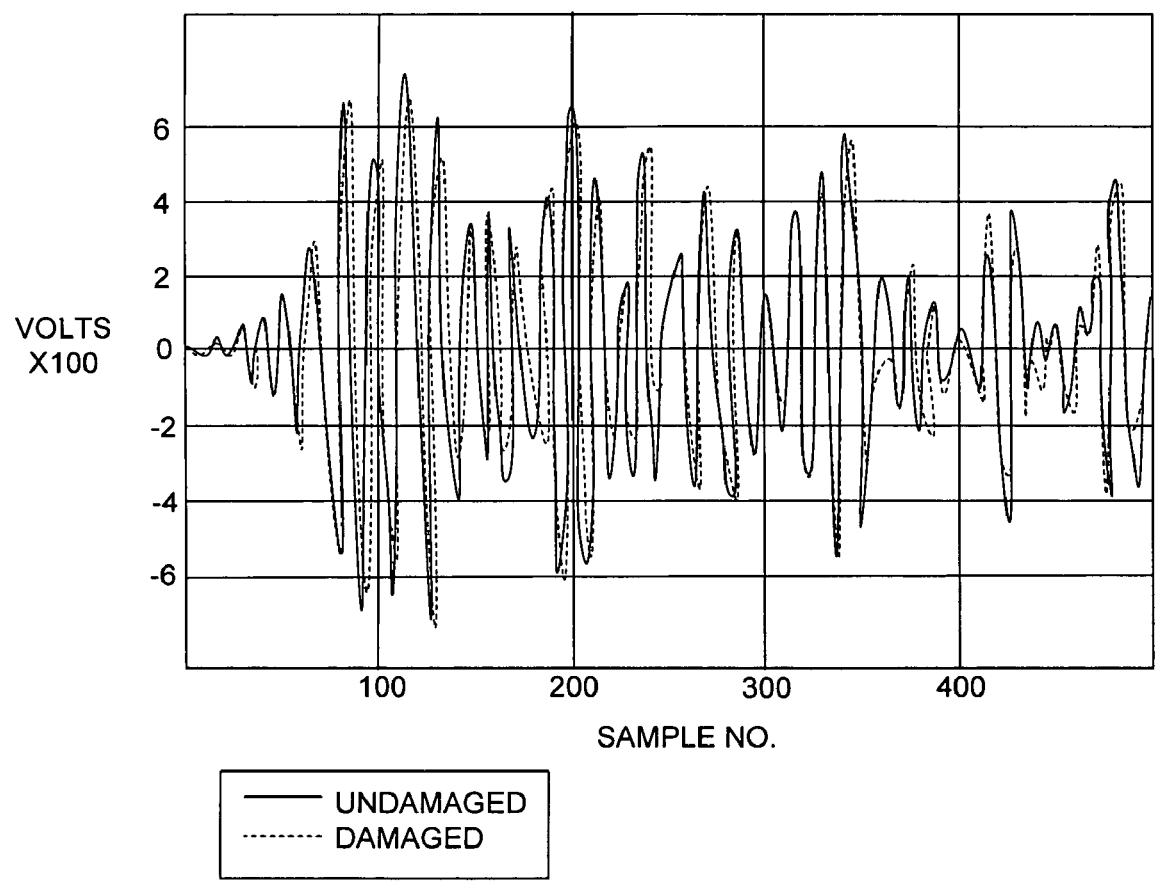
FIG. 3 is a graph showing illustrative baseline measured data and subsequently measured data.

FIG. 3 is a graph showing the baseline measured data and the measured data for the illustrative data of Table 2. As can be seen in FIG. 3, the baseline measured data and the measured data are visibly different. The difference is caused by the flaw in the structure. Due to the flaw, the interference pattern manifested in the baseline measured data is different than the interference pattern manifested in the subsequently measured data. Thus, the baseline measured data and the subsequently measured data are not substantially the same.

After comparing the measured data to the baseline data in step 218, the program outputs the results of the comparison, for example on the display device (step 220). The results include, for example, the data points and/or a graphical representation of the data points for each file. Further, the results can include the changes for corresponding data points and an indication of whether there is a flaw in the structure. Alternatively, the program can display additional or alternative results.

Therefore, methods, systems, and articles of manufacture consistent with the present invention test the structural health of a structure using wave interference patterns. Since methods, systems, and articles of manufacture consistent with the present invention do not rely on injecting waves into a structure to observe its resonant response, less power is required compared to conventional approaches. Further, methods and systems consistent with the present invention are not affected by changing material response due to internal strain on a structure. Therefore, unlike conventional approaches, invalid flaw detection due to changing frequency response is avoided. Further, since measurement and analysis are performed in the time domain, results can be obtained on the fly instead of having to spend a lot of time analyzing frequency response characteristics.

The foregoing description of an implementation of the invention has been presented for purposes of illustration and description. It is not exhaustive and does not limit the invention to the precise form disclosed. Modifications and variations are possible in light of the above teachings or may be acquired from practicing the invention. For example, the described implementation includes software but the present implementation may be implemented as a combination of hardware and software or hardware alone. Further, the illustrative processing steps performed by the program can be executed in an different order than described above, and additional processing steps or fewer processing steps can be incorporated. For example, the program may obtain the baseline measured data and measured data, but the user may personally compare the data to determine whether there is a flaw in the structure. The invention may be implemented with both object-oriented and non-object-oriented programming systems. The scope of the invention is defined by the claims and their equivalents.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method in a data processing system having a program for identifying a flaw in a structure being tested, the method comprising comparing a first interference pattern resulting from a first wave signal and a second wave signal propagating through the structure being tested to a second interference pattern resulting from the first wave signal and the second wave signal propagating through the structure being tested, the second interference pattern being obtained after obtaining the first interference pattern; determining whether there is a flaw in the structure being tested by determining whether the first interference pattern deviates from the second interference pattern by a predetermined variance; and a step of outputting the results of the determination to one of a display or memory.

2. The method of claim 1 further comprising:
obtaining the first interference pattern.

3. The method of claim 1 further comprising:
obtaining the second interference pattern.

4. The method of claim 1 further comprising:
indicating whether there is a flaw in the structure being tested.

5. The method of claim 1 wherein the first wave signal and the second wave signal are introduced into the structure being tested via a first actuator and a second actuator, respectively.

6. The method of claim 5 wherein the first and second actuators are piezoelectric actuators.

7. The method of claim 1 wherein the first and second interference patterns are obtained using a piezoelectric sensor mechanically coupled to the structure being tested.

8. The method of claim 1 wherein the step of comparing the first interference pattern to the second interference pattern comprises comparing the amplitudes of sampled data of the first interference pattern to the amplitudes of corresponding sampled data of the second interference pattern.

9. A computer-readable medium containing instructions that cause a data processing system having a program to perform a method for identifying a flaw in a structure being tested, the method comprising: comparing a first interference pattern resulting from a first wave signal and a second wave signal propagating through the structure being tested to a second interference pattern resulting from the first wave signal and the second wave signal propagating through the structure being tested, the second interference pattern being obtained after obtaining the first interference pattern; determining whether there is a flaw in the structure being tested by determining whether the first interference pattern deviates from the second interference pattern by a predetermined variance; and outputting the results of the determination to one of a display or memory.

10. The computer-readable medium of claim 9 further comprising:
obtaining the first interference pattern.

11. The computer-readable medium of claim 9 further comprising:
obtaining the second interference pattern.

12. The computer-readable medium of claim 9 further comprising:
indicating whether there is a flaw in the structure being tested.

13. The computer-readable medium of claim 9 wherein the first wave signal and the second wave signal are introduced into the structure being tested via a first actuator and a second actuator, respectively.

14. The computer-readable medium of claim 13 wherein the first and second actuators are piezoelectric actuators.

15. The computer-readable medium of claim 9 wherein the first and second interference patterns are obtained using a piezoelectric sensor mechanically coupled to the structure being tested.

16. The computer-readable medium of claim 9 wherein comparing the first interference pattern to the second interference pattern comprises comparing the amplitudes of sampled data of the first interference pattern to the amplitudes of corresponding sampled data of the second interference pattern.

17. A data processing system for identifying a flaw in a structure being tested, the data processing system comprising: a memory having a program that: compares a first interference pattern resulting from a first wave signal and a second wave signal propagating through the structure being tested to a second interference pattern resulting from the first wave signal and the second wave signal propagating through the structure being tested, the second interference pattern being obtained after obtaining the first interference pattern; determines whether there is a flaw in the structure being tested by determining whether the first interference pattern deviates from the second interference pattern by a predetermined variance; and outputs the results of the determination to one of a display or memory; and a processing unit that runs the program.

18. A data processing system for identifying a flaw in a structure being tested, the data processing system comprising: means for comparing a first interference pattern resulting from a first wave signal and a second wave signal propagating through the structure being tested to a second interference pattern resulting from the first wave signal and the second wave signal propagating through the structure being tested, the second interference pattern being obtained after obtaining the first interference pattern; means for determining whether there is a flaw in the structure being tested by determining whether the first interference pattern deviates from the second interference pattern by a predetermined variance; and means for outputting the results of the determination by the means of determining to one of a display or memory.

* * * * *